United States Patent [19]

Molloy et al.

[11] Patent Number: 4,569,801

[45] Date of Patent: Feb. 11, 1986

[54] ALKYLSULFONAMIDOPHENYLALKYLA-MINES

[75] Inventors: Bryan B. Molloy, North Salem; Mitchell I. Steinberg, Indianapolis, both of Ind.

[73] Assignee: Eli Lilly and Company, Indianapolis, Ind.

[21] Appl. No.: 660,816

[22] Filed: Oct. 15, 1984

[51] Int. Cl.$^4$ .................. C07C 143/75; A61K 31/18
[52] U.S. Cl. ..................... 260/501.21; 260/501.19; 260/501.1; 564/99; 514/605
[58] Field of Search .......... 564/99; 260/501.1, 501.19; 514/605

[56] References Cited

U.S. PATENT DOCUMENTS 3,574,741  4/1971  Gould ................................. 564/82
4,289,787  9/1981  Molloy et al. ..................... 424/329
4,336,269  6/1982  Molloy et al. ..................... 424/330

OTHER PUBLICATIONS

Uloth et al., J. of Med. Chem. 9(1), pp. 88–97 1966.
Riggilo et al., J. of Pharmacol. Exp. Ther. 1968 163(1), pp. 25-35.
Somani et al., *The Journal of Pharmacology and Experimental Therapeutics* 164, No. 2, 317 (1968).
Barlow et al., *British Journal of Pharmacology* 37, 555 (1969).
Holland et al., *J. Med. Chem.* 6, 521 (1963).

*Primary Examiner*—Thomas A. Waltz
*Assistant Examiner*—R. A. Picard
*Attorney, Agent, or Firm*—Bruce J. Barclay; Arthur R. Whale

[57] ABSTRACT

The present invention relates to a new class of alkylsulfonamidophenylalkylamines which are potent antiarrhythmic agents having good oral bioavailability properties.

19 Claims, No Drawings

ALKYLSULFONAMIDOPHENYLALKYLAMINES

BACKGROUND OF THE INVENTION

U.S. Pat. No. 4,289,787 describes a group of phenylalkyl quaternary ammonium salts that are useful as antiarrhythmic agents and are effective in prolonging the action potential duration of cardiac tissue. One compound within this group, namely 4-chloro-N,N-diethyl-N-heptylbenzenebutanaminium phosphate, has undergone extensive biological evaluations and is now known generically as clofilium. A summary of the efficacy of this compound is set forth in *New Drugs Annual: Cardiovascular Drugs*, Vol. 2, 103, edited by Alexander Scriabine, Raven Press, New York (1984).

While clofilium and quaternary ammonium salts similar in structure to clofilium have proved to be extremely potent antiarrhythmic agents, their clinical usefulness has been limited in part because of their marginal oral bioavailability. It is now believed that the relatively low order of oral bioavailability is attributable in part to the charged nature of the quaternary ammonium portion of the molecule.

While the quaternary ammonium compounds disclosed in U.S. Pat. No. 4,289,787 are in general much more potent antiarrhythmic agents than the corresponding secondary and tertiary amines from which they are derived, one particular group of secondary and tertiary amines has been reported to possess unexpectedly good antiarrhythmic activity compared to agents such as clofilium; see U.S. Pat. No. 4,336,269. The specific group of compounds claimed in that patent are phenylalkylamines wherein the phenyl group is required to bear a para-nitro substituent.

While the para-nitro phenylalkylamines are extremely potent antiarrhythmic agents which prolong the action potential duration of cardiac tissue, it has now been learned that such nitro compounds are also rapidly metabolized by some biological systems, such as by conscious dog models, to agents having significantly diminished efficacy. One possible product of metabolism may be the corresponding amino substituted phenylalkylamine, which is known to be substantially inactive as an antiarrhythmic agent.

We have now discovered a group of phenyalkylamines that are potent antiarrhythmic agents, that appear to have good oral bioavailability properties and that do not appear to be subject to as rapid inactivation in vivo as the previously described agents. It therefore is an object of this invention to provide a new class of phenylalkylamines that can be employed in the clinical treatment of re-entrant cardiac arrhythmias.

SUMMARY OF THE INVENTION

This invention concerns new chemical compounds characterized as alkylsulfonamido substituted phenylalkylamines. The invention is more particularly directed to a compound of the formula

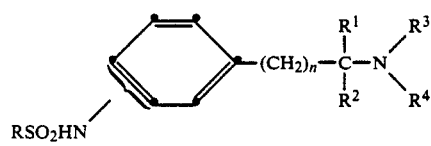

wherein:

R is $C_1$–$C_6$ alkyl;
$R^1$ is hydrogen, methyl or ethyl;
$R^2$ is hydrogen or $C_1$–$C_3$ alkyl;
$R^3$ is hydrogen or $C_1$–$C_8$ alkyl;
$R^4$ is $C_1$–$C_{10}$ alkyl;
n is 2, 3, 4 or 5; and
the pharmaceutically acceptable acid addition salts thereof.

The invention also provides pharmaceutical formulations comprising a compound of the above formula and a pharmaceutically acceptable carrier, diluent or excipient therefor.

A further embodiment of the invention is a method for treating cardiac arrhythmias in mammals comprising administering to a mammal suffering from an arrhythmia or to a mammal suspected of developing an arrhythmia a compound of the above formula.

DETAILED DESCRIPTION OF THE INVENTION

In the above formula, the term $C_1$–$C_6$ alkyl represents a straight or branched chain alkyl bearing from one to six carbon atoms. Typical $C_1$–$C_6$ alkyl groups include methyl, ethyl, n-propyl, isopropyl, n-butyl, sec-butyl, isopentyl, n-hexyl and isohexyl.

The term $C_1$–$C_3$ alkyl represents methyl, ethyl, n-propyl and isopropyl.

$C_1$–$C_8$ Alkyl includes straight and branched chain alkyl such as methyl, ethyl, isopropyl, n-hexyl, 1,1-dimethylhexyl, 1,2-dimethylpentyl and n-octyl.

$C_1$–$C_{10}$ Alkyl includes methyl, ethyl, n-pentyl, isohexyl, 2-ethylheptyl, n-heptyl, 3-methylheptyl, 1,2-dimethylheptyl, 1,2-dimethyloctyl, 1,1-dimethylheptyl, n-nonyl, n-decyl and related alkyl groups.

In a preferred embodiment, R is methyl, n is 3, $R^1$ is hydrogen or methyl, $R^2$ is hydrogen, $R^3$ is $C_2$–$C_4$ alkyl and $R^4$ is $C_2$–$C_{10}$ alkyl. $R^3$ is ideally ethyl or butyl and $R^4$ is preferably heptyl. The sulfonamide group is preferably in the 4-position of the phenyl ring.

As pointed out above, the invention includes the pharmaceutically acceptable acid addition salts of the compounds defined by the above formula. Since the compounds of this invention are secondary and tertiary amines, they are basic in nature and accordingly react with any number of inorganic and organic acids to form pharmaceutically acceptable acid addition salts. Acids commonly employed to form such salts include mineral acids such as hydrochloric, hydrobromic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Preferred pharmaceutically acceptable acid addition salts include those formed with mineral acids such as hydrochloric acid and hydrobromic acid, as well as those formed with organic acids such as oxalic acid and citric acid.

The compounds of the invention are preferably synthesized by reducing a nitrophenyl derivative to the corresponding aminophenyl derivative and acylating the latter compound with an alkylsulfonyl acylating agent. This reaction may be represented by the following scheme:

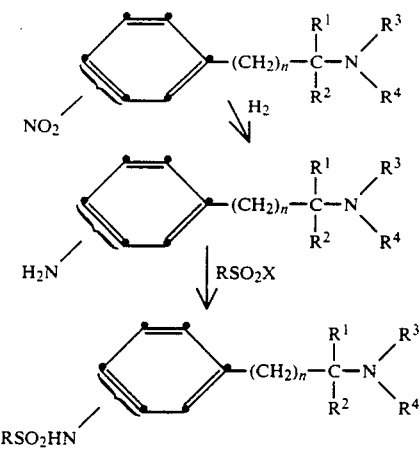

wherein R, R¹, R², R³, R⁴ and n are as defined above and X is a leaving group such as halo, for example chloro or bromo.

The first step of the above described reaction procedure involves the conversion of a nitrophenyl derivative to the corresponding aminophenyl derivative and is conducted by procedures well known to those of ordinary skill in the art. The nitro compound is typically hydrogenated to the amino compound in the presence of hydrogen gas and a catalytically sufficient amount of a suitable catalyst such as Raney nickel, platinum and especially palladium on carbon. A catalytically sufficient amount of catalyst will be in the range of about one-tenth part to about 100 parts by weight of the nitrophenyl derivative to one part of catalyst by weight. It should be noted that greater or lesser quantities of catalyst may be employed if desired depending on the specified conditions.

The reduction is conducted in the presence of hydrogen gas generally at a pressure in the range of from about standard pressure to approximately 100 pounds per square inch. The reaction is substantially complete after about 1 to 24 hours when conducted at a temperature of about 15° C. to about 100° C., more preferably from about 20° C. to about 50° C.

Once the process is complete, the product may be isolated according to standard procedures. Typically the reaction mixture is filtered through infusorial earth to remove the residual catalyst. The filtrate is then normally concentrated under reduced pressure to provide the appropriate aminophenyl derivative. The product thus isolated may then be further purified if desired by employing any one of several common techniques such as crystallization from common solvents such as ethyl acetate or chloroform or column chromatography over solid supports such as silica gel or alumina.

Conversion of the aminophenyl intermediate to the corresponding alkylsulfonamido substituted phenylalkylamine of the invention is conducted by procedures well known in the art. The aminophenyl derivative is preferably reacted with an alkylsulfonyl halide in the presence of an organic solvent and a suitable base capable of acting as an acid scavenger. Typical organic solvents include chloroform, methylene chloride, DMF, benzene, toluene and other like aprotic solvents. Suitable bases include organic bases such as triethylamine and inorganic bases such as sodium bicarbonate or potassium carbonate. When a solvent such as pyridine is employed, as is preferred, no additional acid scavenger need be added. Typically the reaction is substantially complete after about 1 to 72 hours when conducted at a temperature in the range of about 0° C. to about 150° C.

The product thus prepared may be isolated by standard procedures. Typically the volatiles are evaporated under reduced pressure and the residue is stirred in water. The resulting slurry is made basic, for example by the addition of any one of a number of bases such as ammonium hydroxide to a pH in the range of about 8 to 10. The product may be conveniently isolated by extracting the aqueous alkaline solution with a suitable water immiscible organic solvent such as ethyl acetate or chloroform, and evaporating the solvent from the extract. The product thus isolated can be further purified, for example by high pressure liquid chromatography or crystallization, according to standard procedures.

The alkylsulfonamido substituted phenylalkylamines provided by this invention can alternatively be prepared by any number of other general chemical processes. A typical process, for instance, comprises first acylating a primary or secondary alkylsulfonamido substituted phenylalkylamine to form the corresponding amide and then reducing the amide by reaction with a reducing agent such as diborane, sodium borohydride, lithium aluminum hydroxide, or the like. For example, an amine such as N-[4-[4-(methylamino)butyl]phenyl]-methanesulfonamide can be acylated by reaction with an acylating agent such as acetyl chloride to form the corresponding acetamide derivative. Reduction of the amide affords the corresponding amine of this invention, namely, N-[4-[4-(methylethylamino)butyl]phenyl]-methanesulfonamide. Alternatively, an amine such as n-heptylamine can be acylated with a phenylalkanoyl halide such as 3-(4-ethylsulfonamidophenyl)propanoyl chloride to form the corresponding propionamide derivative. Reduction of this amide affords the corresponding amine of the invention. Further acylation with a suitable acylating agent, for example acetyl bromide, followed by reduction gives a tertiary amine of the invention, for instance, N-[4-[3-(ethylheptylamino)-propyl]phenyl]methanesulfonamide.

The pharmaceutically acceptable acid addition salts of the invention are typically formed by reacting a secondary or tertiary amine of the invention with an equimolar or excess amount of acid. The reactants are generally combined in a mutual solvent such as diethyl ether or benzene, and the salt normally precipitates out of solution within about one hour to 10 days, and can be isolated by filtration.

The nitrophenyl derivatives employed as starting materials in the preferred process of the present invention are known in the art and may be prepared by any one of the procedures outlined in U.S. Pat. No. 4,289,787, incorporated herein by reference. The other starting materials employed herein are either commercially available or known and readily prepared by prior art processes.

The following Examples further illustrate the synthesis of compounds of the present invention. The Examples are not intended to be limiting in any respect and should not be so construed.

EXAMPLE 1

N-[4-[4-(Ethylheptylamino)butyl]phenyl]methanesulfonamide ethanedioate

A. N-Ethyl-N-heptyl-4-nitrobenzenebutanamide

A 500 ml round bottom flask fitted with an addition funnel and a calcium sulfate drying tube was charged with 8.0 g (0.03 mol) of 4-(4-nitrophenyl)butyric acid in 180 ml of carbon tetrachloride. To this stirred solution was added 16.5 ml (0.19 mol) of oxalyl chloride dropwise. The addition funnel was removed and a condenser was fitted onto the flask. The reaction mixture was refluxed for 3 hours, cooled and the excess oxalyl chloride was evaporated under reduced pressure. Approximately 100 ml of dry diethyl ether was added to the solution which was subsequently cooled in ice. To this cooled solution was added 16.3 g (0.115 mol) of ethylheptylamine dissolved in approximately 60 ml of diethyl ether. The resulting reaction mixture was stirred at room temperature overnight and diluted with a mixture of water and diethyl ether. The aqueous phase was separated and further extracted three times with diethyl ether. The organic extracts were combined, washed with water, hydrochloric acid, water (2×), a 10% aqueous sodium carbonate solution and a saturated sodium chloride solution. The organic phase was separated, dried over anhydrous sodium sulfate and evaporated to dryness under reduced pressure to provide 12.847 g of N-ethyl-N-heptyl-4-nitrobenzenebutanamide as an oil.

B. N-Ethyl-N-heptyl-4-nitrobenzenebutylaminium oxalate

A 500 ml 3-neck round bottom flask fitted with a glass wool drying tube, thermometer and addition funnel was charged with 114 ml (0.114 mol) of diborane in THF (Aldrich Chemical). To this solution was added a solution of 12.847 g (0.038 mol) of N-ethyl-N-heptyl-4-nitrobenzenebutanamide in 50 ml of THF while maintaining the temperature of the reaction mixture below 30° C. with an external water bath. The reaction mixture was stirred overnight at room temperature and cooled in ice. To the solution cooled in ice was added sufficient 2N hydrochloric acid to decompose any excess diborane and the reaction mixture was concentrated under reduced pressure. The resulting residue was combined with 150 ml of 2N hydrochloric acid and refluxed for approximately 30 minutes. The resulting mixture was cooled and made basic with 5N sodium hydroxide. The alkaline solution was extracted three times with diethyl ether and the organic extracts were combined and washed two times with water, two times with 2N sulfuric acid, four times with water, one time with 5N sodium hydroxide and one time with a saturated sodium chloride solution. The organic phase was dried over anhydrous sodium sulfate and evaporated to dryness under reduced pressure to provide 2.33 g of material which was discarded. The sulfuric acid extract was basified with 5N sodium hydroxide and extracted three times with diethyl ether. The resulting organic phase was washed with saturated sodium chloride solution and dried over anhydrous sodium sulfate to provide, following evaporation under reduce pressure, 10.547 g of material having two spots on the thin-layer chromatography. This material was dissolved in 60 ml of acetic anhydride and 10 drops of acetic acid was added thereto. The reaction mixture was refluxed for 1.5 hours, cooled and slowly poured into 500 ml of ice-water. The mixture was evaporated in vacuo and the residue was dissolved in water, and basified with 5N sodium hydroxide. This mixture was extracted three times with diethyl ether and the resulting organic extracts were combined, washed with water and a saturated sodium chloride solution, dried, and concentrated to provide 10.334 g of N-ethyl-N-heptyl-4-nitrobenzenebutanamine as in oil. This material was dissolved in ethyl acetate and combined with 2.92 g of oxalic acid dissolved in ethyl acetate. The precipitated solid was collected by filtration and recrystallized from approximately 300 ml of ethyl acetate to provide 8.963 g of N-ethyl-N-heptyl-4-nitrobenzenebutylaminium oxalate. mp=115°-117° C.

Analysis calculated for $C_{21}H_{34}N_2O_6$: Theory: C, 61.44; H, 8.35; N, 6.82; Found: C, 61.67; H, 8.48; N, 6.98.

C. 4-Amino-N-ethyl-N-heptylbenzenebutanamine

Four and four-tenths grams of N-ethyl-N-heptyl-4-nitrobenzenebutylaminium oxalate prepared above were converted to the free base with ammonium hydroxide. The aqueous solution was extracted with diethyl ether and the organic phase was concentrated in vacuo to provide 3.466 g of the free base. The free base was dissolved in 95 ml of ethanol and hydrogenated at room temperature for 30 minutes in the presence of 1 g of 5% palladium on carbon. One hundred percent hydrogen uptake was observed. The reaction mixture was filtered through Celite and the filtrate was evaporated to dryness under reduced pressure to provide 3.114 g of 4-amino-N-ethyl-N-heptylbenzenebutanamine. Additional quantities of this material were prepared by the general procedure outlined above.

D. A 250 ml 3-neck round bottom flask fitted with a thermometer, addition funnel, and calcium sulfate drying tube was charged with 4.292 g (0.015 mol) of 4-amino-N-ethyl-N-heptylbenzenebutanamine and 50 ml of pyridine. The reaction mixture was cooled to approximately 10° C. and 1.5 ml (0.019 mol) of methanesulfonyl chloride was added dropwise. The mixture was allowed to stir overnight at room temperature and was evaporated under reduced pressure. The residue was combined with water and the pH of the resulting suspension was adjusted from approximately 5.5 to approximately 9.5 with concentrated ammonium hydroxide. The basic mixture was extracted four times with chloroform and the organic extracts were combined, washed with an aqueous saturated sodium chloride solution, and evaporated to dryness under reduced pressure to provide 5.916 g of material containing N-[4-[4-(ethylheptylamino)butyl]phenyl]methanesulfonamide as an oil. A thin-layer chromatograph of the material indicated the absence of starting material.

The 5.916 g of material prepared above was purified employing high pressure liquid chromatography. The solvent gradient was methylene chloride to 2½% methanol/methylene chloride/1% ammonium hydroxide. Fractions 26-32 were combined and the solvent was evaporated therefrom to provide 4.069 g of material. This material was dissolved in ethyl acetate and 1 g (0.012 mol) of oxalic acid dissolved in ethyl acetate was added thereto. The precipitated solid was collected by filtration and recrystallized from ethyl acetate to provide 3.845 g of product. mp=118°-122° C. This material was recrystallized from ethyl acetate/methanol to provide 3.667 g of N-[4-[4-(ethylheptylamino)butyl]phenyl]methanesulfonamide ethanedioate. mp=120°-122° C.

Analysis calculated for $C_{22}H_{38}N_2O_6S$: Theory: C, 57.62; H, 8.35; N, 6.11; S, 6.99; Found: C, 57.71; H, 8.22; N, 5.92; S, 6.92.

EXAMPLE 2

N-[4-[4-(Ethylheptylamino)pentyl]phenyl]methanesulfonamide 2-hydroxy-1,2,3-propanetricarboxylate

A. 4-Nitrostyrene

A 500 ml 3-neck round bottom flask was fitted with a thermometer and steam distillation apparatus. The flask was charged with 12.5 g (0.054 mol) of 4-nitrophenethyl bromide, 75 ml (0.565 mol) of triethanolamine and 50 ml of water. The reaction mixture was heated to reflux and the mixture was allowed to slowly steam distill. Approximately 100 mg of hydroquinone was added to the distillate collected in order to prevent polymerization. The distillate was extracted three times with diethyl ether and the combined organic phases were washed with water, 1N hydrochloric acid, water, and a saturated sodium chloride solution in sequence. The organic phase was dried over anhydrous sodium sulfate and evaporated to dryness under reduced pressure to provide 7.193 g of 4-nitrostyrene as an oil which solidified upon cooling. Additional quantities of this material were prepared by the general procedure above.

B. α-Acetyl-4-nitrobenzenebutanoic acid, ethyl ester

Seven hundred milligrams of sodium metal were added to 65 ml of absolute ethanol under a nitrogen atmosphere and under agitation in a 500 ml 4-neck round bottom flask fitted with a thermometer, condenser and calcium sulfate drying tube. The mixture was heated to approximately 70° C. in order to completely dissolve the sodium metal and was subsequently cooled to room temperature. The mixture was charged with 19.5 g (0.091 mol) ethyl acetoacetate and 14.1 g (0.095 mol) of 4-nitrostyrene. The reaction mixture was refluxed for approximately 6 hours and stirred at room temperature overnight. The mixture was poured into 1 l. of water containing 4 ml of concentrated hydrochloric acid. The aqueous solution was extracted three times with diethyl ether, and the organic extracts were combined, washed twice with water and once with a saturated sodium chloride solution. The organic phase was dried over anhydrous sodium sulfate and evaporated to dyrness under reduced pressure to provide 26.101 g of the product as an oil. The oil was dissolved in 100 ml of diethyl ether and cooled to approximately 0° C. for about 60 hours. A small amount of solid was collected by filtration and the filtrate was concentrated in vacuo to provide 22.3 g of α-acetyl-4-nitrobenzenebutanoic acid, ethyl ester as an oil in purified form.

C. 5-(4-Nitrophenyl)-2-pentanone

A mixture of 22.3 g (0.080 mol) of α-acetyl-4-nitrobenzenebutanoic acid, ethyl ester in 500 ml of THF was charged with 250 ml of 6N hydrochloric acid and refluxed overnight. The reaction mixture was cooled and evaporated to dryness under reduced pressure. The residue was diluted with water and extracted three times with diethyl ether. The organic extracts were separated, washed twice with 1N sodium hydroxide, three times with water and once with a saturated sodium chloride solution. The organic solution was dried over anhydrous sodium sulfate and evaporated under reduced pressure. The residue was distilled to remove the 4-chlorobutanol. The residue of this distillate was then further distilled through a 6 inch jacketed vigreaux column and fraction 2 therefrom afforded 6.681 g of 5-(4-nitrophenyl)-2-pentanone.

D. N-Ethyl-α-methyl-4-nitrobenzenebutanamine

A 300 ml round bottom flask fitted with a calcium sulfate drying tube was charged with 6.681 g (0.0322 mol) of 5-(4-nitrophenyl)-2-pentanone in 100 ml of methanol. This mixture was charged with 13.2 g (0.161 mol) of ethylamine hydrochloride and 2.03 g (0.0322 mol) of sodium cyanoborohydride. The resulting suspension was stirred at room temperature over the weekend (about 72 hours) and acidified with concentrated hydrochloric acid. The volatiles were evaporated under reduced pressure and 300 ml of water was added to the residue. The mixture was extracted twice with diethyl ether and the organic phase was washed with water and a saturated sodium chloride solution. The organic phase was dried over anhydrous sodium sulfate and evaporated to dryness. This material was discarded. The aqueous phase was basified with 5N sodium hydroxide and extracted three times with diethyl ether. The organic extracts were combined, washed with saturated sodium chloride solution and dried over anhydrous sodium sulfate. Evaporation of the solvent afforded 6.838 g of N-ethyl-α-methyl-4-nitrobenzenebutanamine.

E. N-Ethyl-N-[1-methyl-4-(4-nitrophenyl)butyl]heptanamide

A 500 ml 3-neck round bottom flask fitted with a thermometer and addition funnel was charged with 7.65 g of sodium carbonate and 70 ml of water. To this mixture was added 6.8 g (0.029 mol) of N-ethyl-α-methyl-4-nitrobenzenebutanamine and 70 ml of acetone. The resulting mixture was cooled to slightly below 25° C. and 4.5 ml (0.029 mol) of heptanoyl chloride and 70 ml of acetone were added while maintaining the temperature of the mixture in the range of about 20°-25° C. The suspension was stirred at room temperature overnight and evaporated to dryness under reduced pressure. The residue was slurried in water and extracted three times with diethyl ether. The organic extracts were combined, washed with water, 2N hydrochloric acid, twice with water and finally a saturated sodium chloride solution. The organic phase was dried over anhydrous sodium sulfate and evaporated to dryness under reduced pressure to provide 7.723 g of N-ethyl-N-[1-methyl-4-(4-nitrophenyl)butyl]heptanamide as an oil.

F. N-Ethyl-N-heptyl-α-methyl-4-nitrobenzenebutanamine

A 500 ml 3-neck round bottom flask was fitted with a condenser and glass wool drying tube. The flask was charged with 60 ml of 1M diborane in THF and 7.7 g (0.022 mol) of N-ethyl-N-[1-methyl-4-(4-nitrophenyl)butyl]heptanamide in 50 ml of THF was added dropwise. The resulting reaction mixture was refluxed overnight and cooled. A solution of 25 ml of 2N hydrochloric acid was added dropwise in order to decompose any excess diborane. The mixture was evaporated under reduced pressure and an additional 150 ml of 2N hydrochloric acid was added. This mixture was refluxed for 1 hour, cooled and made basic with 5N sodium hydroxide. The mixture was extracted three times with diethyl ether and the organic phase was washed with water and a saturated sodium chloride solution. The organic phase was dried over sodium sulfate and evaporated to dryness to provide 7.389 g of N-ethyl-N-heptyl-α-methyl-4-nitrobenzenebutanamine as an oil.

G. N-Ethyl-N-heptyl-α-methyl-4-aminobenzenebutanamine

A mixture of 7.389 g (0.022 mol) of N-ethyl-N-heptyl-α-methyl-4-nitrobenzenebutanamine in 92 ml of ethanol was hydrogenated at room temperature overnight in the presence 0.74 g of 5% palladium-on-carbon. A total of 87% of theoretical hydrogen uptake was observed. The reaction mixture was filtered through Celite and the filtrate was evaporated to dryness under reduced pressure to provide 6.312 g of N-ethyl-N-heptyl-α-methyl-4-aminobenzenebutanamine as an oil.

H. A 250 ml 3-neck round bottom flask fitted with a thermometer, addition funnel and calcium sulfate drying tube was charged with 6.3 g (0.021 mol) of N-ethyl-N-heptyl-α-methyl-4-aminobenzenebutanamine and 90 ml of dry pyridine. The resulting mixture was cooled to 15° C. with an external ice bath and 2.2 ml (0.026 mol) methanesulfonyl chloride was added thereto while maintaining the temperature below approximately 15° C. The external cooling was removed and the reaction mixture was stirred overnight at room temperature. The volatiles were evaporated under reduced pressure and water was added to the residue. The pH of the mixture was adjusted from about 5.7 to about 9 with concentrated ammonium hydroxide. The aqueous phase was extracted three times with chloroform and the organic extracts were combined and washed with saturated sodium chloride solution. The organic phase was dried over anhydrous sodium sulfate and concentrated to provide 9.045 g of a black oil.

The resulting material was purified employing high pressure liquid chromatography. Fractions 31-35 containing 3.289 g of material were combined with 1.98 g of citric acid monohydrate in ethyl acetate. The precipitated solid was collected by filtration and recrystallized from ethanol/acetone (95:5 v:v) to provide 4.516 g of N-[4-[4-(ethylheptylamino)pentyl]phenyl]methanesulfonamide 2-hydroxy-1,2,3-propanetricarboxylate. mp=73°-76° C.

Analysis calculated for $C_{27}H_{38}N_2O_9S$: Theory: C, 56.43; H, 8.07; N, 4.87; S, 5.58; Found: C, 56.70; H, 7.86; N, 4.76; S, 5.34.

EXAMPLE 3

N-[4-[4-(Butylheptylamino)butyl]phenyl]methanesulfonamide ethanedioate

A. N-Butyl-N-heptyl-4-aminobenzenebutanamine

N-Butyl-N-heptyl-4-nitrobenzenebutylaminium oxalate (12.01 g, 0.027 mol) was converted to the free base by slurring this compound in diethyl ether and ammonium hydroxide. The organic phase was separated and evaporated under reduced pressure to provide 9.519 g (0.027 mol) of the free base. This material was combined with a 139 ml of methanol and hydrogenated at room temperature overnight in the presence of 1 g of 5% palladium-on-carbon. The hydrogen uptake observed was 88% of theoretical. The reaction mixture was filtered through Celite and concentrated under vacuum. The residue was dissolved in ether and evaporated to dryness under reduced pressure to provide 8.584 g of N-butyl-N-heptyl-4-aminobenzenebutanamine.

B. A 250 ml 3-neck round bottom flask fitted with a thermometer, addition funnel, and calcium sulfate drying tube was charged with 8.5 g (0.027 mol) of N-butyl-N-heptyl-4-aminobenzenebutanamine and 90 ml of dry pyridine. The reaction mixture was cooled to a temperature of about 10°-15° C. and 2.6 ml (0.034 mol) of methanesulfonyl chloride was added thereto while maintaining the temperature below approximate 15° C. The external ice bath was removed and the reaction mixture was stirred overnight at room temperature. The volatiles were evaporated under reduced pressure and the pH of the reaction mixture was raised to about 9 by the addition of water and concentrated ammonium hydroxide. The aqueous solution was extracted four times with chloroform and the organic extracts were combined, washed with a saturated sodium chloride solution and dried over anhydrous sodium sulfate. The organic phase was concentrated to provide 12.246 g of N-[4-[4-(butylheptylamino)butyl]phenyl]methanesulfonamide as an oil.

The resulting product as prepared above was purified by high pressure liquid chromatography. Fractions 26-32 were combined and the solvent was evaporated therefrom to provide 6.01 g of material. This material was dissolved in ethyl acetate and 1.43 g of oxalic acid dissolved in ethyl acetate was added thereto. The precipitated solid was collected by filtration and recrystallized twice from ethyl acetate to 2.934 g of N-[4-[4-(butylheptylamino)butyl]phenyl]methanesulfonamide ethanedioate. mp=49°-52° C.

Analysis calculated for $C_{24}H_{42}N_2O_6$: Theory: C, 59.23; H, 8.70; N, 5.76; S, 6.59; Found: C, 59.47; H, 8.48; N, 5.74; S, 6.58.

EXAMPLE 4

N-[4-[4-(Butylheptylamino)pentyl]phenyl]methanesulfonamide

A. 4-Amino-N-butyl-N-heptyl-α-methylbenzenebutanamine

A solution of 16.2 g (0.045 mol) of N-butyl-N-heptyl-α-methyl-4-nitrobenzenebutanamine in 182 ml of ethanol was hydrogenated at room temperature overnight in the presence of 1.6 g of 5% palladium-on-carbon. Hydrogen uptake observed was 74% of theoretical. The reaction mixture was filtered through Celite and the filtrate was evaporated under reduced pressure. The resulting material indicated the presence of one spot by thin-layer chromatography and afforded 13.56 g of 4-amino-N-butyl-N-heptyl-α-methylbenzenebutanamine as an oil.

B. A 250 ml 3-neck round bottom flask fitted with a thermometer, calcium sulfate drying tube and addition funnel was charged with 13.56 g (0.041 mol) of 4-amino-N-butyl-N-heptyl-α-methylbenzenebutanamine in 175 ml of dry pyridine. The reaction mixture was cooled to approximately 15° C. and 4.15 ml (0.052 mol) of methanesulfonyl chloride was added thereto while maintaining the temperature of the reaction mixture below approximately 15° C. The reaction mixture was stirred at room temperature overnight and the volatiles were evaporated under reduced pressure. The residue was slurried in water and the pH was adjusted from about 5.4 to approximately 10 with concentrated ammonium hydroxide. The aqueous solution was extracted three times with chloroform and the organic extracts were combined, washed twice with water and once with a saturated sodium chloride solution. The organic phase was dried over anhydrous sodium sulfate and evaporated under reduced pressure to afford 23.159 g of an oil.

The oil thus obtained was purified by high pressure liquid chromatography. Fractions containing the major component were combined and the solvent was evaporated therefrom. The residue was distilled at a pressure of 0.02 mm, and the fraction boiling from about 225° C. to about 240° C. was collected to provide 4.619 g of N-[4-[4-(butylheptylamino)pentyl]phenyl]methanesulfonamide.

Analysis calculated for $C_{23}H_{42}N_2O_2S$: Theory: C, 67.27; H, 10.31; N, 6.82; S, 7.81; Found: C, 67.09; H, 10.08; N, 6.93; S, 7.61.

EXAMPLE 5

N-[4-[4-(Ethylheptylamino)butyl]phenyl]methanesulfonamide monohydrobromide

N-[4-[4-(ethylheptylamino)butyl]phenyl]methanesulfonamide (5.56 g, 0.015 mol), prepared according to the general procedure outlined in Example 1, was dissolved in diethyl ether. The solution was cooled with a dry ice/acetone bath and diethyl ether saturated with hydrogen bromide gas was added thereto. The volatiles were evaporated under reduced pressure and 100 ml of ethyl acetate was added to the residue. The solution was triturated and appoximately 6 grams of crystals were collected. The solid was recrystallized from isopropyl alcohol to provide 2.5 g of N-[4-[4-(ethylheptylamino)butyl]phenyl]methanesulfonamide monohydrobromide. mp=98°–100° C. Yield 37%

Analysis calculated for $C_{20}H_{37}BrN_2O_2S$: Theory: C, 53.44; H, 8.30; N, 6.23; S, 7.13; Br, 17.78; Found: C, 53.66; H, 8.57; N, 6.23; S, 7.00; Br, 17.59.

The following compounds were prepared according to the general procedures outlined above.

EXAMPLE 6

N-[4-[4-(Ethylheptylamino)butyl]phenyl]methanesulfonamide 4-methylbenzenesulfonate, mp=101°–103° C.

Analysis calculated for $C_{27}H_{44}N_2O_5S_2$: Theory: C, 59.97; H, 8.20; N, 5.18; S, 11.86; Found: C, 60.18; H, 8.03; N, 5.10; S, 11.85.

EXAMPLE 7

N-[3-[4-(Ethylheptylamino)butyl]phenyl]methanesulfonamide, bp=215° C./0.03 mm

Analysis calculated for $C_{20}H_{36}N_2O_2S$: Theory: C, 65.17; H, 9.85; N, 7.60; S, 8.70; Found: C, 64.92; H, 9.58; N, 7.73; S, 8.96.

EXAMPLE 8

N-[4-[4-(Ethylheptylamino)butyl]phenyl]ethanesulfonamide, bp=205°–220° C./0.03 mm Analysis calculated for $C_{21}H_{38}N_2O_2S$: Theory: C, 65.92; H, 10.01; N, 7.32; Found: C, 65.86; H, 9.82; N, 7.03.

EXAMPLE 9

N-[4-[3-(Dimethylamino)propyl]phenyl]methanesulfonamide, mp=108°–111° C.

Analysis calculated for $C_{12}H_{28}N_2O_2S$: Theory: C, 56.22; H, 7.86; N, 10.93; Found: C, 56.30; H, 7.86; N, 10.86.

EXAMPLE 10

N-[4-[4-(Butylheptylamino)pentyl]phenyl]methanesulfonamide monohydrobromide, mp=99°–101° C.

Analysis calculated for $C_{23}H_{43}BrN_2O_2S$: Theory: C, 56.20; H, 8.82; N, 5.70; Br, 16.25; S, 6.52; Found: C, 56.39; H, 8.64; N, 5.60; Br, 16.48; S, 6.46.

EXAMPLE 11

N-[4-[4-(Ethylheptylamino)butyl]phenyl]methanesulfonamide monohydrochloride, mp=99°–101° C.

Analysis calculated for $C_{20}H_{37}ClN_2O_2S$: Theory: C, 59.31; H, 9.21; N, 6.92; Cl, 8.75; S, 7.92; Found: C, 59.55; H, 9.07; N, 7.01; Cl, 8.95; S, 8.02.

As noted above, the compounds of this invention are useful in treating and preventing re-entrant arrhythmias. Therefore, another embodiment of the present invention is a method for treating arrhythmia in mammals which comprises administering to a mammal suffering from an arrhythmia and in need of treatment or to a mammal suspected of developing an arrhythmia a pharmaceutically effective amount of a compound of the invention.

The term "pharmaceutically effective amount", as used herein, represents an amount of a compound of the invention which is capable of treating or preventing re-entrant arrhythmias. The particular dose of compound administered according to this invention will of course be determined by the particular circumstances surrounding the case, including the compound administered, the route of administration, the particular arrhythmia being treated, and similar considerations. The compounds can be administered by a variety of routes including the oral, rectal, transdermal, subcutaneous, intravenous, intramuscular or intranasal routes. It is a special feature of the compounds that they have good oral bioavailability without losing their substantial potent antiarrhythmic effect. A typical single dose for prophylactic treatment, however, will contain from about 0.2 mg/kg to about 20 mg/kg of the active compound of this invention when administered orally. Preferred oral doses will be about 0.5 to about 10 mg/kg, ideally about 1 to about 5 mg/kg. When a present compound is given orally it may be necessary to administer the compound more than once each day, for example about every eight hours. For IV administration by bolus, the dose will be from about 1.0 μg/kg to about 3000 μg/kg, preferably about 50 μg/kg to about 500 μg/kg.

The compounds of the present invention are particularly important due to their potent and selective ability to prolong the action potential duration of cardiac tissue. The compounds of the invention accordingly are useful in the treatment of arrhythmia by decreasing the vulnerability of the heart to re-entrant atrial and ventricular rhythms and atrial and ventricular fibrillation by prolonging the time of electrical systole. Since the compounds enhance the electrical stability of the heart, they are useful in combination with external electrical devices intended to terminate tachyarrhythmias, for instance ventricular tachycardia and ventricular fibrillation.

The compounds provided herein are effective in converting atrial and ventricular flutter, fibrillation, or rapid tachycardia to normal sinus rhythm as a result of the prolongation of refractoriness of both atrial and ventricular tissues. The compounds are useful in situations where rapid inappropriate ventricular rates are present, particularly in cases of ventricular preexcitation tachyarrhythmia. The compounds are preferably utilized for the control of re-entrant arrhythmias in humans and for the prevention of sudden death resulting from ventricular fibrillation. Accordingly it is contemplated that the compounds are best utilized in a prophylactic treatment.

It is well known that the more homogeneous repolarization, the less likely one is to incur recurrent re-entrant arrhythmias. Excessive prolongation of the Qtc interval is generally indicative of non-homogeneous repolarization of cardiac cells within the heart. An unexpected advantage of the present compounds is that when administered intravenously they have the ability to lessen the prolongation of the Qtc interval for a given increase in refractoriness as compared to other known antiarrhythmic agents such as clofilium, as disclosed in U.S. Pat. No. 4,289,787, and those agents as disclosed in U.S. Pat. No. 4,277,501.

The compounds of the present invention are preferably formulated prior to administration. Therefore, yet another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

Formulation 1

Hard gelatin capsules are prepared using the following ingredients:

|  | Quantity (mg/capsule) |
|---|---|
| N—[4-[4-(Ethylheptylamino)butyl]phenyl]methanesulfonamide ethanedioate | 250 |
| Starch, dried | 200 |
| Magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/tablet) |
|---|---|
| N—[4-[4-(Butylheptylamino)butyl]phenyl]methanesulfonamide ethanedioate | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight % |
|---|---|
| N—[4-[4-(Ethylheptylamino)pentyl]phenyl]methanesulfonamide 2-hydroxy-1,2,3-propanetricarboxylate | 0.25 |
| Ethanol | 29.75 |
| Propellant 22 | 70.00 |
| (Chlorodifluoromethane) |  |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made up as follows:

|  |  |
|---|---|
| N—[4-[4-(Butylheptylamino)pentyl]phenyl]methanesulfonamide | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

| | |
|---|---|
| N—[4-[4-(Ethylheptylamino)-butyl]phenyl]methanesulfonamide | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities. Such oral formulation is well suited for patients receiving treatment from electrical defibrillation devices.

Formulation 6

Suppositories each containing 225 mg of active ingredient may be made as follows:

| | |
|---|---|
| N—[4-[4-(Ethylheptylamino)-butyl]phenyl]ethanesulfonamide | 225 mg |
| Saturated fatty acid glycerides to | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| | |
|---|---|
| N—[4-[3-(dimethylamino)propyl]-phenyl]methanesulfonamide | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| | |
|---|---|
| N—[3-[4-(ethylheptylamino)-butyl]phenyl]methanesulfonamide | 100 mg |
| isotonic saline | 1000 ml |

The solution of the above ingredients is administered intravenously at a rate of 1 ml per minute to a subject suffering from ventricular fibrillation.

The antiarrhythmic activity of the compounds provided by the present invention was determined by the use of standard electrophysiological techniques to measure resting potential, action potential amplitude, duration, rate of rise and effective refractory periods of normal canine Purkinje fibers superfused in vitro with Ringer's solution at 35° C. and driven at a constant frequency of 1 Hz. Table 1 presents the data obtained for a number of compounds of the invention when evaluated in this test. The data presented is the percent increase in the action potential duration at 95% of full repolarization at $10^{-7}$M.

TABLE 1

| Compound of Example No. | Percent Increase in Action Potential Duration |
|---|---|
| 1 | 31 ± 6 |
| 3 | 26 ± 4 |
| 7 | 20 ± 9 |
| 8 | 19 ± 4 |

The present compounds are also active in the conscious dog model, in contrast to those compounds disclosed in U.S. Pat. No. 4,277,501.

Certain of the compounds of the present invention were tested in halothane-anesthetized dogs in an effort to evaluate the effectiveness of the compounds in increasing the ventricular effective refractory period. Table 2 provides the quantity of specified compound in mg/kg necessary to increase the aforementioned refractory period by 30 msec. when administered either intravenously or intraduadenally. The compounds were tested against clofilium and N-ethyl-N-heptyl-4-nitrobenzenebutanamine, ethanedioic acid for comparative purposes.

TABLE 2

| Compound | Intraduodenal mg/kg | Intravenous mg/kg | I.D./I.V. |
|---|---|---|---|
| Example 1 | 2.2 | 0.29 | 8 |
| Example 2 | 8.0 | 0.27 | 30 |
| Example 3 | 2.4 | 0.10 | 24 |
| Example 4 | 4.0 | 0.25 | 16 |
| clofilium | 7.0 | 0.18 | 39 |
| N—ethyl-N—heptyl-4-nitrobenzenebutanamine, ethanediotic acid | 1.1 | 0.06 | 18 |

We claim:

1. A compound of the formula wherein:
R is $C_1$-$C_6$ alkyl;

$R^1$ is hydrogen, methyl or ethyl;
$R^2$ is hydrogen or $C_1$–$C_3$ alkyl;
$R^3$ is hydrogen or $C_1$–$C_8$ alkyl;
$R^4$ is $C_1$–$C_{10}$ alkyl;
n is 2, 3, 4 or 5; and
the pharmaceutically acceptable acid addition salts thereof.

2. A compound of claim 1 wherein R is methyl.

3. A compound of claim 2 wherein $R^3$ is $C_2$–$C_4$ alkyl.

4. A compound of claim 3 wherein $R^4$ is $C_2$–$C_{10}$ alkyl.

5. A compound of claim 4 wherein both $R^1$ and $R^2$ are hydrogen.

6. The compound of claim 5 which is N-[4-[4-(ethylheptylamino)butyl]phenyl]methanesulfonamide, and its pharmaceutically acceptable acid addition salts.

7. The compound of claim 6 which is N-[4-[4-(ethylheptylamino)butyl]phenyl]methanesulfonamide ethanedioate.

8. The compound of claim 6 which is N-[4-[4-(ethylheptylamino)butyl]phenyl]methanesulfonamide monohydrobromide.

9. The compound of claim 6 which is N-[4-[4-(ethylheptylamino)butyl]phenyl]methanesulfonamide benzenesulfonate.

10. The compound of claim 6 which is N-[4-[4-(ethylheptylamino)butyl]phenyl]methanesulfonamide monohydrochloride.

11. The compound of claim 5 which is N-[4-[4-(butylheptylamino)butyl]phenyl]methanesulfonamide and it pharaceutically acceptable acid addition salts.

12. The compound of claim 11 which is N-[4-[4-(butylheptylamino)butyl]phenyl]methanesulfonamide ethanedioate.

13. A compound of claim 4 wherein one of $R^1$ and $R^2$ is hydrogen and the other is methyl.

14. The compound of claim 13 which is N-[4-[4-(ethylheptylamino)pentyl]phenyl]methanesulfonamide and its pharmaceutically acceptable acid addition salts.

15. The compound of claim 14 which is N-[4-[4-(ethylheptylamino)pentyl]phenyl]methanesulfonamide 2-hydroxy-1,2,3-propanetricarboxylate.

16. The compound of claim 13 which is N-[4-[4-(butylheptylamino)pentyl]phenyl]methanesulfonamide, and its pharmaceutically acceptable acid addition salts.

17. The compound of claim 16 which is N-[4-[4-(butylheptylamino)pentyl]phenyl]methanesulfonamide monohydrobromide.

18. A pharmaceutical formulation comprising an effective antiarrythmic amount of a compound of claim 1 and a pharmaceutically acceptable carrier, diluent or excipient therefor.

19. The formulation of claim 18 wherein the compound is N-[4-[4-(ethylheptylamino)butyl]phenyl]methanesulfonamide, and its pharmaceutically acceptable acid addition salts.

* * * * *